US008673253B2

(12) United States Patent
Chaumonnot et al.

(10) Patent No.: US 8,673,253 B2
(45) Date of Patent: Mar. 18, 2014

(54) AMORPHOUS SILICON-CONTAINING MATERIAL WITH HIERARCHICAL POROSITY

(75) Inventors: Alexandra Chaumonnot, Lyons (FR); Aurelie Coupe, Noisiel (FR); Clement Sanchez, Gif-sur-Yvette (FR); Cedric Boissiere, Paris (FR)

(73) Assignee: IFP Energies Nouvelles, Rueil-Malmaison Cedex (FR)

( * ) Notice: Subject to any disclaimer, the term of this patent is extended or adjusted under 35 U.S.C. 154(b) by 814 days.

(21) Appl. No.: 12/676,707

(22) PCT Filed: Aug. 18, 2008

(86) PCT No.: PCT/FR2008/001198
§ 371 (c)(1),
(2), (4) Date: Oct. 25, 2010

(87) PCT Pub. No.: WO2009/056710
PCT Pub. Date: May 7, 2009

(65) Prior Publication Data
US 2011/0039102 A1 Feb. 17, 2011

(30) Foreign Application Priority Data

Sep. 7, 2007 (FR) ...................................... 07 06296

(51) Int. Cl.
*C01B 33/113* (2006.01)
*C01B 33/12* (2006.01)
(52) U.S. Cl.
USPC ............................. 423/325; 423/335; 428/402
(58) Field of Classification Search
None
See application file for complete search history.

(56) References Cited

U.S. PATENT DOCUMENTS

2006/0030477 A1    2/2006  Chaumonnot et al.

FOREIGN PATENT DOCUMENTS

EP    1 627 853  A1    2/2006

OTHER PUBLICATIONS

International Search Report of PCT/FR2008/001198 (Jun. 5, 2009).
L. Huang et al., "Hierarchical Porous Structures by Using Zeolite Nanocrystals as Building Blocks", Microporous and Mesoporous Materials, vol. 48 (2001) pp. 73-78.
V. Naydenov et al., "Self-Bonded Zeolite Beta/MCM-41 Composite Spheres", Journal of Porous Materials, vol. 12 (2005) pp. 193-199.
J. C. Groen et al., "Mechanism of Hierarchical Porosity Development in MFI Zeolites by Desilication: The Role of Aluminium as a Pore-Directing Agent", Chem. Eur. J., vol. 11 (2005) pp. 4983-4994.
B. Zhang et al., "Starch Gel Templating of Spongelike Macroporous Silicalite Monoliths and Mesoporous Films", Chem. Mater., vol. 14 (2002) pp. 1369-1375.
V. P. Valtchev et al., "Equisetum Arvense Templating of Zeolite Beta Macrostructures with Hierarchical Porosity", Chem. Mater., vol. 16 (2004) pp. 1350-1355.
W. C. Li et al., "Hierarchically Structured Monolithic Silicalite-1 Consisting of Crystallized Nanoparticles and Its Performance in the Beckmann Rearrangement of Cyclohexanone Oxime", J. Am. Chem. Soc., vol. 127 (2005) pp. 12595-12600.
R. Takahashi et al., "Synthesis of Monolithic Zeolites with Macropores", Journal of the Ceramic Society of Japan, vol. 114, No. 5 (2006) pp. 421-424.

*Primary Examiner* — Melvin C Mayes
*Assistant Examiner* — Colin W Slifka
(74) *Attorney, Agent, or Firm* — Millen, White, Zelano & Branigan, P.C.

(57) ABSTRACT

Material with hierarchical porosity consisting of at least two elementary spherical particles having a maximum diameter of 200 microns, at least one of said spherical particles comprising at least one matrix based on silicon oxide, said material having a macropore volume measured by mercury porosimetry ranging between 0.05 and 1 ml/g, a mesopore volume measured by nitrogen volumetric analysis ranging between 0.01 and 1 ml/g and a micropore volume measured by nitrogen volumetric analysis ranging between 0.03 and 0.4 ml/g, said matrix having amorphous walls. The preparation of said material is also described.

21 Claims, No Drawings

AMORPHOUS SILICON-CONTAINING MATERIAL WITH HIERARCHICAL POROSITY

FIELD OF THE INVENTION

The present invention relates to the field of materials containing silicon, notably metallosilicate materials and more precisely aluminosilicate materials, with hierarchical porosity in the microporosity, mesoporosity and macroporosity domains. It also relates to the preparation of these materials that are obtained by means of the synthesis technique referred to as aerosol synthesis.

BACKGROUND OF THE INVENTION

New synthesis strategies allowing to obtain materials of well-defined porosity in a very wide range, from microporous materials to macroporous materials to hierarchical porosity materials, i.e. having pores of several sizes, have known a very large development within the scientific community since the mid-90s (G. J. de A. A. Soler-Illia, C. Sanchez, B. Lebeau, J. Patarin, Chem. Rev., 2002, 102, 4093). In particular, considerable work has been done on the development of materials having a microporosity of zeolitic nature and a mesoporosity so as to simultaneously benefit from the catalytic properties specific to zeolites and from the catalytic and especially the textural properties of the mesoporous phase.

A technique that is commonly used to generate materials having such biporosity consists in directly creating mesopores within zeolite crystals by subjecting the zeolite to a steam-hydrothermal treatment, also referred to as steaming. Under the effect of this treatment, the mobility of the tetrahedric atoms that make up the framework of the zeolite is increased to such an extent that some of these atoms are extracted from the network, which causes formation of amorphous zones that can be cleared to give way to mesoporous cavities (A. H. Jansen, A. J. Koster, K. P. de Jong, J. Phys. Chem. B, 2002, 106, 11905). The formation of such cavities can also be obtained by subjecting the zeolite to an acid treatment (H. Ajot, J. F. Joly, J. Lynch, F. Raatz, P. Caullet, Stud. Surf. Sci. Catal., 1991, 62, 583). These methods however have the drawback of making part of the zeolite partly amorphous and of modifying the properties thereof through variation of the chemical composition. In any case, the mesoporosity thus introduced allows to eliminate or at least to limit diffusion limitation problems encountered in microporous materials, mesopores having much greater diffusion factors than micropores and thus allowing access to the active sites of the zeolites (P. B. Weisz, Chemtech, 1973, 3, 498).

More recently, much work has been done on the elaboration of mixed mesostructured/zeolite materials, mesostructured materials affording the additional advantage of a perfectly organized and calibrated porosity in the mesopore range.

It can be briefly reminded here that mesostructured materials are conventionally obtained via synthesis methods referred to as soft chemistry methods that consist in bringing together, in an aqueous solution or in polar solvents, inorganic precursors with structuring agents, generally molecular or macromolecular surfactants, ionic or neutral. Control of electrostatic interactions or of interactions through hydrogen bonds between the inorganic precursors and the structuring agent jointly linked with hydrolysis/condensation reactions of the inorganic precursor leads to a cooperative assembly of the organic and inorganic phases generating micellar aggregates of surfactants of uniform and controlled size within an inorganic matrix. Clearance of the porosity is then obtained by surfactant elimination, which is conventionally carried out by means of chemical extraction processes or by thermal treatment. Depending on the nature of the inorganic precursors and of the structuring agent used, and on the operating conditions applied, several families of mesostructured materials have been developed, such as the M41S family obtained using long-chain quaternary ammonium salts as the structuring agent (J. S. Beck, J. C. Vartuli, W. J. Roth, M. E. Leonowicz, C. T. Kresge, K. D. Schmitt, C. T.-W. Chu, D. H. Olson, E. W. Sheppard, S. B. McCullen, J. B. Higgins, J. L. Schlenker, J. Am. Chem. Soc., 1992, 114, 27, 10834) or the SBA family obtained using three-block copolymers as the structuring agent (D. Zhao, J. Feng, Q. Huo, N. Melosh, G. H. Fredickson, B. F. Chmelka, G. D. Stucky, Science, 1998, 279, 548).

Several synthesis techniques allowing elaboration of such mixed mesostructured/zeolite materials have thus been listed in the open literature. A first synthesis technique consists in synthesizing in a first stage a mesostructured aluminosilicate material according to the conventional methods described above, then, in a second stage, in impregnating this material with a structuring agent commonly used in the synthesis of zeolitic materials. A suitable hydrothermal treatment leads to a zeolitization of the amorphous walls of the initial mesostructured aluminosilicate (K. R. Koletstra, H. van Bekkum, J. C. Jansen, Chem. Commun., 1997, 2281; D. T. On, S. Kaliaguine, Angew. Chem. Int. Ed., 2001, 40, 3248; D. T. On, D. Lutic, S. Kaliaguine, Micropor. Mesopor. Mater., 2001, 44, 435; M. J. Verhoef, P. J. Kooyman, J. C. van der Waal, M. S. Rigutto, J. A. Peters, H. van Bekkum, Chem. Mater, 2001, 13, 683; S. Kaliaguine, D.T. On, U.S. Pat. No. 6,669,924 B1, 2003). A second synthesis technique consists in bringing together a colloidal solution of zeolite seeds (also referred to as protozeolite entities) and a surfactant commonly used to create a mesostructuration of the final material. The basic idea here is to simultaneously generate the elaboration of an inorganic matrix of organized mesoporosity and the growth, within this matrix, of zeolite seeds so as to ideally obtain a mesostructured aluminosilicate material with crystallized walls (Z. Zhang et al., J. Am. Chem. Soc., 2001, 123, 5014; Y. Liu et al, J. Am. Chem. Soc., 2000, 122, 8791). A variant of these two techniques consists in starting from a mixture of aluminium and silicon precursors in the presence of two structuring agents, one likely to generate a zeolitic system and the other likely to generate a mesostructuration. This solution is then subjected to two crystallization stages under variable hydrothermal treatment conditions, the first stage leading to the formation of the mesoporous structure of organized porosity and the second stage leading to the zeolitization of the amorphous walls (A. Karlsson, M. Stöcker, R. Schmidt, Micropor. Mesopor. Mater., 1999, 27, 181; L. Huang, W. Guo, P. Deng, Z. Xue, Q. Li, J. Phys., Chem. B, 2000, 104, 2817). All of these synthesis methods have the drawback of damaging the mesostructure and thus to lose the advantages thereof in cases where growth of the zeolite seeds or zeolitization of the walls is not perfectly controlled, which makes these techniques delicate to implement.

It can be noted that it is also possible to directly elaborate composite mesostructured/zeolite materials so as to take advantage of the catalytic properties specific to each one of these phases. This can be done through thermal treatment of a mixture of a zeolite seed solution and of a mesostructured aluminosilicate seed solution (P. Prokesova, S. Mintova, J. Cejka, T. Bein, Micropor. Mesopor. Mater., 2003, 64, 165) or through growth of a zeolite layer at the surface of a presynthesized mesostructured aluminosilicate (D. T. On, S. Kaliaguine, *Angew. Chem. Int. Ed.*, 2002, 41, 1036).

To the exclusion of the mesoporous zeolitic materials obtained through post-treatment of a zeolite, we note that, from an experimental point of view, all these materials are obtained by direct precipitation of inorganic precursors in the presence or not of structuring agents within an aqueous solution or in polar solvents, this stage being in most cases followed by one or more ripening stages in an autoclave. The elementary particles usually obtained exhibit no regular shape and they are generally characterized by a size ranging between 200 and 500 nm.

Work has also been done on the elaboration of materials exhibiting both microporosity and macroporosity. By way of example, one of the most commonly used synthesis methods consists in using polystyrene balls as the macroporosity-generating element and in creating around these balls a zeolitic network (G. S. Zhu, S. L. Qiu, F. F. Gao, D. S. Li, Y. F. Li, R. W. Wang, B. Gao, B. S. Li, Y. H. Guo, R. R. Xu, Z. Liu, O. Terasaki, *J. Mater. Chem.*, 2001, 11, 6, 1687).

SUMMARY OF THE INVENTION

The invention relates to a material with hierarchical porosity consisting of at least two elementary spherical particles having a maximum diameter of 200 microns, at least one of said spherical particles comprising at least one matrix based on silicon oxide, said material having a macropore volume measured by mercury porosimetry ranging between 0.05 and 1 ml/g, a mesopore volume measured by nitrogen volumetric analysis ranging between 0.01 and 1 ml/g and a micropore volume measured by nitrogen volumetric analysis ranging between 0.03 and 0.4 ml/g, said matrix having amorphous walls that consist of zeolite seeds at the origin of the microporosity of the material.

Said matrix based on silicon oxide optionally also comprises at least one element X selected from among aluminium, iron, boron, indium and gallium, preferably aluminium. The present invention also relates to the preparation of the material according to the invention. The method of preparing the material according to the invention comprises:
a) preparing a clear solution containing the precursor elements of zeolite seeds, i.e. at least one structuring agent, at least one silicic precursor and optionally at least one precursor of at least one element X selected from among aluminium, iron, boron, indium and gallium; b) mixing into a solution at least one surfactant and at least said clear solution obtained in stage a); c) aerosol atomizing said solution obtained in stage b) so as to lead to the formation of spherical droplets; d) drying said droplets; and e) eliminating said structuring agent and said surfactant so as to obtain an amorphous material with hierarchical porosity in the microporosity, mesoporosity and macroporosity domains.

The microporosity induced by the amorphous walls of the material according to the invention results not only from the use of a solution comprising the zeolite seed precursor elements according to stage a) of the method of the invention, but also from aerosol atomizing the solution comprising at least one surfactant and a clear solution according to stage c) of the method of the invention. The mesoporosity and the macroporosity of the material according to the invention result from the phenomenon of phase separation through spinodal decomposition of the organic phase generated by the presence of the surfactant and of the inorganic phase from the solution containing the zeolite seed precursor elements, this phase separation phenomenon being induced by the technique known as aerosol technique according to stage c) of the method of the invention.

Interest of the Invention

The material according to the invention that comprises a mesoporous and macroporous inorganic matrix, based on silicon oxide, with microporous and amorphous walls, simultaneously exhibits the textural properties specific to microporous materials, to mesoporous materials and to macroporous materials. Preferably, the matrix based on silicon oxide forming each one of the elementary spherical particles of the material according to the invention comprises, in addition to silicon, at least one element X selected from among aluminium, iron, indium and gallium, preferably aluminium, so as to form an amorphous aluminosilicate matrix. The material according to the invention then exhibits, when X is aluminium, greater acidobasicity properties than the amorphous aluminosilicate materials of the prior art, devoid of zeolite precursors, and prepared according to synthesis protocols known to the person skilled in the art using inorganic silica and alumina precursors. Besides, the presence, within the same spherical particle of micrometric or even nanometric size, of mesopores and macropores in a microporous and amorphous inorganic matrix leads to preferential access of the reactants and of the reaction products to the microporous sites when the material according to the invention is used as adsorbent or acidic solid in potential industrial applications. Furthermore, the material according to the invention consists of spherical elementary particles, the diameter of these particles being maximum 200 µm, preferably less than 100 µm, advantageously ranging between 50 nm and 20 µm, more advantageously between 50 nm and 10 µm and most advantageously between 50 nm and 300 nm. The limited size of these particles and their homogeneous spherical shape provides better diffusion of the reactants and of the reaction products when the material according to the invention is used in potential industrial applications by comparison with materials known from the prior art that come in form of elementary particles of non-homogeneous shape, i.e. irregular, and of size often above 500 nm.

DETAILED DESCRIPTION

The object of the present invention is a material with hierarchical porosity consisting of at least two elementary spherical particles having a maximum diameter of 200 microns, at least one of said spherical particles comprising at least one matrix based on silicon oxide and having amorphous walls, said material having a macropore volume measured by mercury porosimetry ranging between 0.05 and 1 ml/g, a mesopore volume measured by nitrogen volumetric analysis ranging between 0.01 and 1 ml/g and a micropore volume measured by nitrogen volumetric analysis ranging between 0.03 and 0.4 ml/g.

What is understood to be a material with hierarchical porosity, in the sense of the present invention, is a material having at least one and generally more spherical particle(s) with triple porosity: a macroporosity characterized by a macropore mercury volume ranging between 0.05 and 1 ml/g, preferably between 0.1 and 0.3 ml/g, a mesoporosity characterized by a mesopore volume measured by nitrogen volumetric analysis ranging between 0.01 and 1 ml/g, preferably between 0.1 and 0.6 ml/g, and a microporosity induced by the amorphous walls, the characteristics of the microporosity depending on the constituent zeolite seeds of the amorphous walls of the matrix of each spherical particle of the material according to the invention. The macroporosity is also characterized by the presence of macroporous domains ranging from 50 to 1000 nm, preferably from 80 to 500 nm and/or it results from an intraparticular textural macroporosity; the mesoporosity is also characterized by the presence of mesoporous domains ranging from 2 to 50 nm, preferably from 10 to 50 nm. The material according to the invention can also advantageously have elementary spherical particles devoid of mesoporosity. It can be noted that a porosity of microporous nature can also result from the imbrication of the surfactant, used in the preparation of the material according to the invention, with the inorganic wall at the level of the organic-inorganic interface developed upon elaboration of said material according to the invention.

In accordance with the invention, the matrix based on silicon oxide forming each of the spherical particles of the material according to the invention has amorphous walls consisting of zeolite seeds that are at the origin of the microporosity present within each spherical particle of the material according to the invention. Zeolite seeds are species prepared from reactants used for the synthesis of zeolites whose preparation has not been brought to the crystallized zeolite formation stage. Said small-size seeds are therefore not detected when characterized by wide-angle X-ray diffraction. More precisely and in accordance with the invention, the zeolite seeds that make up the amorphous microporous walls of the matrix of each spherical particle of the material according to the invention are species that can serve as a primer for the synthesis of any zeolite known to the person skilled in the art and, in particular, but in a non-exhaustive manner, the synthesis of the zeolites listed in *"Atlas of zeolite framework types"*, 5$^{th}$ revised Edition, 2001, C. Baerlocher, W. M. Meier, D. H. Olson, bringing into a solution the precursor elements of the zeolite seeds, i.e. at least one structuring agent, at least one silicic precursor and optionally at least one precursor of at least one element X selected from among aluminium, iron, boron, indium and gallium, preferably aluminium, being such that it leads to a clear solution. The zeolite seeds that make up the amorphous walls of the matrix of each particle of the material according to the invention and at the origin of the microporosity thereof preferably are species for priming at least one zeolite selected from among the following zeolites: ZSM-5, ZSM-48, ZSM-22, ZSM-23, ZBM-30, EU-2, EU-11, Silicalite, Beta, zeolite A, Faujasite, Y, USY, VUSY, SDUSY, mordenite, NU-87, NU-88, NU-86, NU-85, IM-5, IM-12, Ferrierite and EU-1. More preferably, the zeolite seeds that make up the amorphous walls of the matrix of each particle of the material according to the invention are species for priming at least one zeolite selected from among the zeolites of MFI, BEA, FAU and LTA structural type.

In accordance with the invention, the matrix based on silicon oxide forming each of the elementary spherical particles of the material according to the invention is either entirely silicic or it comprises, in addition to silicon, at least one element X selected from among aluminium, iron, boron, indium and gallium, preferably aluminium. Thus, the zeolite seeds that make up the amorphous walls of the matrix of each particle of the material according to the invention and at the origin of the microporosity thereof advantageously are species for priming at least one zeolite, either entirely silicic or containing, in addition to silicon, at least one element X selected from among aluminium, iron, boron, indium and gallium, preferably aluminium. When X is aluminium, the matrix of the material is in this case an amorphous aluminosilicate, precursor of a crystallized aluminosilicate material. This amorphous aluminosilicate has a Si/Al molar ratio identical to that of the solution of the silicic and aluminic precursors leading to the formation of the zeolite seeds that make up the amorphous walls of the matrix. Said elementary spherical particles making up the material according to the invention are devoid of zeolite nanocrystals.

In accordance with the invention, said elementary spherical particles making up the material according to the invention have a maximum diameter of 200 microns, preferably less than 100 microns, advantageously ranging between 50 nm and 20 µm, more advantageously ranging between 50 nm and 10 µm, and most advantageously ranging between 50 and 300 nm. More precisely, they are present in the material according to the invention in form of aggregates.

The material according to the invention advantageously has a specific surface area ranging between 100 and 1100 m$^2$/g, more advantageously between 200 and 800 m$^2$/g.

The object of the present invention also is the preparation of the material according to the invention. Said method of preparing the material according to the invention comprises: a) preparing a clear solution containing the precursor elements of zeolite seeds, i.e. at least one structuring agent, at least one silicic precursor and optionally at least one precursor of at least one element X selected from among aluminium, iron, boron, indium and gallium, preferably aluminium; b) mixing into a solution at least one surfactant and at least said clear solution obtained in stage a); c) aerosol atomizing said solution obtained in stage b) so as to lead to the formation of spherical droplets; d) drying said droplets; and e) eliminating said structuring agent and said surfactant so as to obtain an amorphous material with hierarchical porosity in the microporosity, mesoporosity and macroporosity domains.

In accordance with stage a) of the preparation method according to the invention, the clear solution containing the zeolite seed precursor elements, i.e. at least one structuring agent, at least one silicic precursor and optionally at least one precursor of at least one element X selected from among aluminium, iron, boron, indium and gallium, preferably aluminium, is produced from operating protocols known to the person skilled in the art.

The silicic precursor used for carrying out stage a) of the method according to the invention is selected from among the silicon oxide precursors known to the person skilled in the art. In particular, a silicic precursor selected from among the silica precursors commonly used in the synthesis of zeolites is advantageously used, for example powdered solid silica, silicic acid, colloidal silica, dissolved silica or tetraethoxysilane, also referred to as tetraethylorthosilicate (TEOS). The silicic precursor preferably is TEOS.

The precursor of element X optionally used for carrying out stage a) of the method according to the invention can be any compound comprising element X and that can release this element in solution, notably in aqueous or aquo-organic solution, in reactive form. In the preferred case where X is aluminium, the aluminic precursor advantageously is an inorganic aluminium salt of formula AlZ$_3$, Z being a halogen, a nitrate or a hydroxide. Preferably, Z is chlorine. The aluminic precursor can also be an aluminium sulfate of formula Al$_2$(SO$_4$)$_3$. The aluminic precursor can also be an organometallic precursor of formula Al(OR)$_3$ where R=ethyl, isopropyl, n-butyl, s-butyl (Al(O$^s$C$_4$H$_9$)$_3$) or t-butyl or a chelated precursor such as aluminium acetylacetonate (Al(C$_5$H$_8$O$_2$)$_3$). Preferably, R is s-butyl. The aluminic precursor can also be sodium or ammonium aluminate, or alumina proper, in one of its crystalline phases known to the person skilled in the art (alpha, delta, teta, gamma), preferably in hydrated form or in a form that can be hydrated.

It is also possible to use mixtures of the aforementioned precursors. Some or all of the aluminic and silicic precursors can optionally be added in form of a single compound comprising both aluminium atoms and silicon atoms, an amorphous silica alumina for example.

The structuring agent used for carrying out stage a) of the method according to the invention can be ionic or neutral depending on the nature of the zeolite obtained from said zeolite seeds. The structuring agents from the following non-exhaustive list are frequently used: nitrogen-containing organic cations such as tetrapropylammonium (TPA), elements from the alkaline family (Cs, K, Na, etc.), crown ethers, diamines, as well as any other structuring agent known to the person skilled in the art for zeolite synthesis.

The clear solution containing the zeolite seed precursor elements according to stage a) of the material preparation method of the invention is generally obtained by preparing a reaction mixture containing at least one silicic precursor, optionally at least one precursor of at least one element X selected from among aluminium, iron, boron, indium and gallium, preferably at least one aluminic precursor, and at least one structuring agent. The reaction mixture is either aqueous or aquo-organic, a water-alcohol mixture for example. A basic reaction medium is preferably used throughout the various stages of the method according to the invention in order to favour the development of the zeolite seeds making up the amorphous walls of the matrix of each particle of the material according to the invention. The basicity of the solution is advantageously provided by the basicity of the structuring agent used or by basification of the reaction mixture through addition of a basic compound, for example an alkaline metal hydroxide, preferably sodium hydroxide. The reaction mixture can be subjected to hydrothermal conditions under autogenous pressure, optionally by adding a gas, nitrogen for example, at a temperature ranging between ambient temperature and 200° C., preferably between ambient temperature and 170° C., more preferably at a temperature that does not exceed 120° C. until formation of a clear solution containing the precursor elements of the zeolite seeds that make up the amorphous walls of the matrix of each spherical particle of the material according to the invention. According to a preferred method of operation, the reaction mixture containing at least one structuring agent, at least one silicic precursor and optionally at least one precursor of at least one element X selected from among aluminium, iron, boron, indium and gallium is ripened at ambient temperature so as to obtain a clear solution containing the precursor elements of zeolite seeds likely to generate the formation of crystallized zeolite entities.

In accordance with stage a) of the method according to the invention, the precursor elements of the zeolite seeds present in the clear solution are synthesized according to operating protocols known to the person skilled in the art. In particular, for a material according to the invention the matrix of each particle of which consists of beta zeolite seeds, a clear solution containing precursor elements of beta zeolite seeds is prepared according to the operating protocol described by P. Prokesova, S. Mintova, J. Cejka, T. Bein et al., *Micropor. Mesopor. Mater.*, 2003, 64, 165. For a material of the invention the matrix of each spherical particle of which consists of Y zeolite seeds, a clear solution containing precursor elements of Y zeolite seeds is prepared according to the operating protocol described by Y. Liu, W. Z. Zhang, T. J. Pinnavaia et al., *J. Am. Chem. Soc.*, 2000, 122, 8791. For a material according to the invention the matrix of each spherical particle of which consists of faujasite zeolite seeds, a clear solution containing precursor elements of faujasite zeolite seeds is prepared from the operating protocols described by K. R. Kloetstra, H. W. Zandbergen, J. C. Jansen, H. vanBekkum, *Microporous Mater.*, 1996, 6, 287. For a material according to the invention the matrix of each spherical particle of which consists of ZSM-5 type zeolite seeds, a clear solution containing precursor elements of ZSM-5 zeolite seeds is prepared from the operating protocol described by A. E. Persson, B. J. Schoeman, J. Sterte, J.-E. Otterstedt, *Zeolites*, 1995, 15, 611, the exact operating protocol being the object of Example 1 of the present application. In the particular case of a purely silicic material, the clear solution containing the precursor elements of silicalite zeolite seeds making up the walls of said material of the invention is advantageously prepared according to the operating protocol described by A. E. Persson, B. J. Schoeman, J. Sterte, J.-E. Otterstedt, *Zeolites*, 1994, 14, 557.

In accordance with stage b) of the material preparation method according to the invention, the surfactant used is an ionic or a non-ionic surfactant or a mixture thereof. Preferably, the ionic surfactant is selected from among anionic surfactants such as sulfates, like for example sodium dodecylsulfate (SDS). Preferably, the non-ionic surfactant can be any copolymer having at least two parts of different polarities conferring amphiphilic macromolecule properties on them. These copolymers can belong to the non-exhaustive list of the following copolymer families: fluorinated copolymers (—[$CH_2$—$CH_2$—$CH_2$—$CH_2$—O—CO—R1-with R1=$C_4F_9$, $C_8F_{17}$, etc.), biological copolymers such as polyamino acids (poly-lysine, alginates, etc.), dendrimers, block copolymers consisting of poly(alkylene oxide) chains and any other copolymer of amphiphilic character known to the person skilled in the art (S. Förster, M. Antionnetti, *Adv. Mater,* 1998, 10, 195-217; S. Förster, T. Plantenberg, *Angew. Chem. Int. Ed,* 2002, 41, 688-714; H. Cölfen, *Macromol. Rapid Commun,* 2001, 22, 219-252).

Preferably, a block copolymer consisting of poly(alkylene oxide) chains is used within the scope of the present invention. Said block copolymer is preferably a block copolymer having two, three or four blocks, each block consisting of a poly(alkylene oxide) chain. For a two-block copolymer, one of the block consists of a poly(alkylene oxide) chain of hydrophilic nature and the other block consists of a poly(alkylene oxide) chain of hydrophobic nature. For a three-block copolymer, at least one of the blocks consists of a poly(alkylene oxide) chain of hydrophilic nature whereas at least one of the other blocks consists of a poly(alkylene oxide) chain of hydrophobic nature. Preferably, in the case of a three-block copolymer, the poly(alkylene oxide) chains of hydrophilic nature are poly(ethylene oxide) chains denoted by $(PEO)_x$ and $(PEO)_z$, and the poly(alkylene oxide) chains of hydrophobic nature are poly(propylene oxide) chains denoted by $(PPO)_y$, poly(butylene oxide) chains or mixed chains each chain of which is a mixture of several alkylene oxide monomers. More preferably, in the case of a three-block copolymer, a compound consisting of two poly(ethylene oxide) chains and of one poly(propylene oxide) chain is used, and more particularly a compound of formula $(PEO)_x$-$(PPO)_y$-$(PEO)_z$ where x ranges between 5 and 300, y ranges between 33 and 300, and z ranges between 5 and 300. Preferably, the values of x and z are identical. A compound wherein x=20, y=70 and z=20 (P123) and a compound wherein x=106, y=70 and z=106 (F127) are very advantageously used. The commercial non-ionic surfactants known as Pluronic (BASF), Tetronic (BASF), Triton (Sigma), Tergitol (Union Carbide) and Brij (Aldrich) can be used as non-ionic surfactants in stage b) of the preparation method according to the invention. For a four-block copolymer, two of the blocks consist of a poly (alkylene oxide) chain of hydrophilic nature and the other two blocks consist of a poly(alkylene oxide) chain of hydrophobic nature.

The solution obtained at the end of stage b) of the preparation method according to the invention wherein at least said surfactant and at least said clear solution obtained in stage a) are mixed can be acid, neutral or basic. Preferably, said solution is basic and it preferably has a pH value above 9, this pH value being generally imposed by the pH value of the clear solution containing the precursor elements of zeolite seeds obtained according to stage a) of the material preparation method of the invention. The solution obtained at the end of stage b) can be aqueous or it can be a mixture of water and organic solvent, the organic solvent preferably being a polar solvent, notably an alcohol, preferably ethanol.

The amount of surfactant introduced in the mixture in accordance with stage b) of the preparation method according to the invention is defined in relation to the amount of inorganic matter introduced into said mixture upon adding the clear solution containing the precursor elements of zeolite seeds obtained according to stage a) of the method of the invention. The amount of inorganic matter corresponds to the amount of matter of the silicic precursor and of the precursor of element X when it is present. The $n_{inorganic}/n_{surfactant}$ molar ratio is such that the organic-inorganic binary system formed in atomization stage c) of the preparation method according to the invention undergoes a phase separation characterized by the appearance of an interconnected two-phase network whose formation mechanism is a spinodal decomposition. The decomposition domain for which a phase separation occurs through a spinodal decomposition mechanism is delimited by bounds for which the free enthalpy G of the binary system is minimized ($\partial G/\partial x=0$, x being the molar fraction of the organic phase, 1-x that of the inorganic phase) and, for each composition belonging to this domain, the second derivative of the enthalpy $\partial^2 G/\partial^2 x$ is greater than 0. The principle of phase separation via a spinodal decomposition mechanism has been widely described by Nakanishi for obtaining silica gels in the presence of polymers (K. Nakanishi, *Journal of Porous Materials*, 1997, 4, 67). The particular interconnection of the two-phase organic-inorganic network resulting from this phase separation phenomenon through spinodal decomposition is at the origin of the particular mesoporous and macroporous texture exhibited by the material according to the invention. In accordance with stage b) of the method according to the invention, the initial concentration of the surfactant introduced in the mixture, defined by $c_0$, is such that $c_0$ is less than or equal to $c_{mc}$, parameter $c_{mc}$ representing the critical micellar concentration known to the person skilled in the art, i.e. the limit concentration beyond which the phenomenon of self-assembly of the surfactant molecules occurs in the solution. Prior to atomization, the surfactant molecule concentration of the solution defined by stage b) of the preparation method according to the invention does therefore not lead to the formation of particular micellar phases. In a preferred embodiment of the method according to the invention, concentration $c_0$ is less than $c_{mc}$, ratio $n_{inorganic}/n_{surfactant}$ is such that the composition of the binary system verifies the composition conditions for which a phase separation mechanism takes place through spinodal decomposition and said solution sought in stage b) of the preparation method according to the invention is a basic water-alcohol mixture.

The mixture atomization stage according to stage c) of the preparation method according to the invention produces spherical droplets. The size distribution of these droplets is of lognormal type. The aerosol generator used here is a commercial device of 9306 A type provided by TSI having a 6-jet atomizer. Atomization of the solution occurs in a chamber into which a carrier gas, a $O_2/N_2$ mixture (dry air), is sent at a pressure P of 1.5 bar.

In accordance with stage d) of the preparation method according to the invention, said droplets are dried. Drying is carried out through the transportation of said droplets via the carrier gas, the $O_2/N_2$ mixture, in PVC tubes, which leads to the progressive evaporation of the solution, for example the basic aquo-organic solution obtained in stage b) of the preparation method according to the invention, and thus to the formation of spherical elementary particles. This drying procedure is completed by passage of said particles through an oven whose temperature can be adjusted, the usual temperature ranging between 50° C. and 600° C., preferably between 80° C. and 400° C., the residence time of these particles in the oven being of the order of one second. The particles are then recovered on a filter. A pump arranged at the end of the circuit favours delivery of the species in the aerosol experimental device. Drying of the droplets according to stage d) of the preparation method of the invention is advantageously followed by passage through a stove at a temperature ranging between 50° C. and 150° C.

In the particular case where element X optionally used for carrying out stage a) of the method according to the invention is the element aluminium and where the element sodium is present in the clear solution obtained in accordance with stage a) of the preparation method according to the invention via the use of sodium hydroxide and/or of a sodium-containing structuring agent providing the basicity of said clear solution, an additional stage of ionic exchange allowing the $Na^+$ cation to be exchanged for the $NH_4^+$ cation between stages d) and e) of the invention is preferably carried out. This exchange, which leads to the formation of $H^+$ protons after stage e) of the preparation method of the invention in the preferred case where elimination of the structuring agent and of the surfactant is performed by calcination in air, is carried out according to operating protocols known to the person skilled in the art. One of the usual methods consists in suspending the dried solid particles from stage d) of the preparation method of the invention in an aqueous solution of ammonium nitrate. The assembly is then brought to reflux for 1 to 6 hours. The particles are thereafter recovered by filtering (9000 rpm centrifugation), washed and then dried through passage in the stove at a temperature ranging between 50° C. and 150° C. This ion exchange/washing/drying cycle can be repeated several times and preferably two more times. This exchange cycle can also be performed after stages d) and e) of the method according to the invention. Under these conditions, stage e) is then repeated after the last exchange cycle so as to generate the $H^+$ protons as explained above.

In accordance with stage e) of the preparation method of the invention, elimination of the structuring agent and of the surfactant in order to obtain the material according to the invention with hierarchical porosity is advantageously carried out by means of chemical extraction methods or thermal treatment, preferably by calcination in air in a temperature range between 300° C. and 1000° C., preferably between 400° C. and 600° C., for 1 to 24 hours, preferably for 2 to 12 hours.

If the solution prepared in stage b) of the method according to the invention is a water-organic solvent mixture, preferably basic, it is essential that, during stage b) of the method, the surfactant concentration be lower than the critical micellar concentration and that ratio $n_{inorganic}/n_{surfactant}$ be such that the variation of the free enthalpy of mixing $\Delta G_m$ and the second derivative of the free enthalpy $\partial^2 G/\partial^2 x$ are greater than 0, so that the evaporation of said aquo-organic solution, preferably basic, during stage c) of the preparation method according to the invention by means of the aerosol technique induces a phenomenon of organic and inorganic phase separation through spinodal decomposition leading to the generation of the mesoporous and macroporous phases of the spherical particles of the material according to the invention. Said observed phase separation is the result of a progressive concentration, within each droplet, of the silicic precursor, optionally of the precursor of element X, preferably of the aluminic precursor and of the surfactant resulting from an evaporation of the aquo-organic solution, preferably basic, until a sufficient reactant concentration is reached to cause said phenomenon.

The material with hierarchical porosity according to the present invention can be obtained in form of powder, balls, pellets, granules or extrudates, the shaping operations being performed using conventional techniques known to the person skilled in the art. Preferably, the material with hierarchical porosity according to the invention is obtained in form of a powder consisting of elementary spherical particles having a maximum diameter of 200 µm, which facilitates a possible reactant diffusion if the material according to the invention is used in a potential industrial application.

The material with hierarchical porosity according to the invention is characterized by means of several analysis techniques, notably nitrogen volumetric analysis (BET), mercury porosimetry, transmission electron microscopy (TEM), scanning electron microscopy (SEM) and X-ray fluorescence (XRF).

Nitrogen volumetric analysis, which corresponds to the physical adsorption of nitrogen molecules in the porosity of the material via a progressive pressure increase at constant temperature, provides information on the particular textural characteristics (pore diameter, porosity type, specific surface area) of the material according to the invention. In particular, it allows to know the total value of the micropore and mesopore volume of the material. The shape of the nitrogen adsorption isotherm and of the hysteresis loop can give information about the presence of the microporosity linked with the zeolite seeds making up the amorphous walls of the matrix of each spherical particle of the material according to the invention and about the nature of the mesoporosity. Quantitative analysis of the microporosity of the material according to the invention is carried out from the "t" (Lippens-De Boer method, 1965) or the "$\alpha_s$" (method provided by Sing) methods that correspond to transforms of the initial adsorption isotherm as described in *"Adsorption by powders and porous solids. Principles, methodology and applications"* written by F. Rouquerol, J. Rouquerol and K. Sing, Academic Press, 1999. These methods allow in particular to obtain the value of the micropore volume characteristic of the microporosity of the material according to the invention, as well as the specific surface area of the sample. The reference solid used is a LiChrospher Si-1000 silica (M. Jaroniec, M. Kruck, J. P. Olivier, *Langmuir*, 1999, 15, 5410). By way of example, the nitrogen adsorption isotherm of a material of mesoporous and macroporous porosity, the microporous matrix walls of each spherical particle of which consist of ZSM-5 (MFI) zeolite seeds, obtained according to the material preparation method of the invention using TEOS as the silicic precursor, $Al(O^sC_4H_9)_3$ as the aluminic precursor, TPAOH as the structuring agent and the particular block copolymer known as poly(ethylene oxide)$_{106}$-poly(propylene oxide)$_{70}$-poly(ethylene oxide)$_{106}$ ($PEO_{106}$-$PPO_{70}$-$PEO_{106}$ or F127) as the surfactant, exhibits a great adsorption jump in the P/P0 low values range (where P0 is the saturated vapour pressure at temperature T), followed by a plateau with a very slight slope over a wide pressure range, characteristic of a microporous material, as well as a type IV isotherm and a type H1 hysteresis loop in the high values range of P/P0 representative of mesopores whose size ranges between 2 and 50 nm. Similarly, curve $V_{ads}$ (ml/g)=f($\alpha_s$) obtained via the aforementioned $\alpha_s$ method is characteristic of the presence of microporosity within the material and it leads to a micropore volume value ranging between 0.03 and 0.4 ml/g. Determination of the total micropore and mesopore volume and of the micropore volume as described above leads to a mesopore volume value for the material according to the invention ranging between 0.01 and 1 ml/g.

Mercury porosimetry analysis corresponds to the intrusion of a volume of mercury characteristic of the existence of mesopores and of macropores in the material of the invention according to the ASTM D4284-83 standard at a maximum pressure of 4000 bars, using a surface tension of 484 dyne/cm and a contact angle of 140° (value selected following those recommended in "Technique de l'ingénieur, traité analyse et caractérisation", page 1050, written by J. Charpin and B. Rasneur), assuming that the pores are of cylindrical shape. This technique is perfectly well suited for analysis of mesoporous and macroporous samples as a complement to the nitrogen volumetric analysis technique described above. In particular, this technique allows to obtain the mesoporous mercury volume value ($V_{Hgmeso}$ in ml/g) defined as the mercury volume adsorbed by all of the pores whose diameter is in the mesopore range, i.e. ranging between 3.6 and 50 nm (value of the upper bound as defined according to the IUPAC standard). Similarly, the macroporous mercury volume ($V_{Hgmacro}$ in ml/g) is defined as the mercury volume adsorbed by all of the pores whose diameter is greater than or equal to 50 nm. By way of example, the mercury porosimetry analysis of a material of mesoporous and macroporous porosity, the microporous matrix walls of each spherical particle of which consist of ZSM-5 (MFI) zeolite seeds, obtained according to the method of the invention using TEOS as the silicic precursor, $Al(O^sC_4H_9)_3$ as the aluminic precursor, TPAOH as the structuring agent and the particular block copolymer known as poly(ethylene oxide)$_{106}$-poly(propylene oxide)$_{70}$-poly(ethylene oxide)$_{106}$ ($PEO_{106}$-$PPO_{70}$-$PEO_{106}$ or F127) as the surfactant leads to a mesoporous mercury volume ranging between 0.01 and 1 ml/g and to a macroporous mercury volume ranging between 0.05 and 1 ml/g.

Transmission electron microscopy (TEM) analysis is also a commonly used technique for characterizing the mesoporosity and the macroporosity of the material according to the invention. TEM allows formation of an image of the solid studied, the contrasts observed being characteristic of the structural organization, the texture, the morphology or the chemical composition of the particles observed, and the resolution of the technique reaches 0.2 nm maximum. In the description hereafter, the TEM photos are obtained from michrotome sections of the sample in order to visualize a section of an elementary spherical particle of the material according to the invention. For example, the TEM images obtained for a material of mesoporous and macroporous porosity whose microporous walls consist of ZSM-5 (MA) zeolite seeds obtained according to the material preparation method of the invention using TEOS as the silicic precursor, $Al(O^sC_4H_9)_3$ as the aluminic precursor, TPAOH as the structuring agent and the particular block copolymer known as poly(ethylene oxide)$_{106}$-poly(propylene oxide)$_{70}$-poly(ethylene oxide)$_{106}$ ($PEO_{106}$-$PPO_{70}$-$PEO_{106}$ or F127) as the surfactant, exhibit within the same spherical particle a mesoporosity and a macroporosity characteristic of an organic-inorganic phase separation through a spinodal decomposition mechanism following atomization stage c) of the material preparation method according to the invention whose domain size ranges between 15 and 50 nm and between 100 and 400 nm respectively.

The morphology and the size distribution of the elementary particles were established by analysis of photos obtained by scanning electron microscopy (SEM).

The present invention also relates to the use of the material with hierarchical porosity according to the invention as an adsorbent for pollution control or as molecular sieve for separation. The object of the present invention thus also is an adsorbent comprising the material with hierarchical porosity according to the invention. It is also advantageously used as a catalyst, notably an acid catalyst, in reactions such as those conducted in the spheres of refining and petrochemistry for example.

When the material with hierarchical porosity according to the invention is used as a catalyst, this material can be associated with an inorganic matrix that can be inert or catalytically active and with a metallic phase. The inorganic matrix can be present simply as a binder to hold together the particles of said material in the various known catalyst forms (extrudates, pellets, balls, powders), or it can be added as a diluent to impose a degree of conversion in a process that would otherwise progress too rapidly, thus leading to catalyst fouling as a result of the formation of a large amount of coke. Typical inorganic matrices are notably supporting materials for catalysts, such as the various forms of silica, alumina, silica-alumina, magnesia, zirconia, as well as titanium, boron oxides, aluminium, titanium, zirconium phosphates, clays such as kaolin, bentonite, montmorilionite, sepiolite, attapulgite, fuller's earth, synthetic porous materials such as $SiO_2$—$Al_2O_3$, $SiO_2$—$ZrO_2$, $SiO_2$—$ThO_2$, $SiO_2$—$BeO$, $SiO_2$—$TiO_2$ or any combination of these compounds. The inorganic matrix can be a mixture of various compounds, in particular of an inert phase and of an active phase. Said material of the present invention can also be associated with at least one zeolite and act as the main active phase or as an additive. The metallic phase can be introduced entirely on said material of the invention. It can also be introduced entirely on the inorganic matrix or on the assembly consisting of the inorganic matrix and the material with hierarchical porosity by ion exchange or impregnation with cations or oxides selected from among the following elements: Cu, Ag, Ga, Mg, Ca, Sr, Zn, Cd, B, Al, Sn, Pb, V, P, Sb, Cr, Mo, W, Mn, Re, Fe, Co, Ni, Pt, Pd, Ru, Rh, Os, Ir and any other element of the periodic table of elements.

The catalytic compositions comprising the material of the present invention are generally well suited for implementation of the main hydrocarbon conversion processes and organic compound synthesis reactions.

The catalytic compositions comprising the material of the invention advantageously find applications in the following reactions: isomerization, transalkylation and dismutation, alkylation and dealkylation, hydration and dehydration, oligomerization and polymerization, cyclization, aromatization, cracking, reforming, hydrogenation and dehydrogenation, oxidation, halogenation, hydrocracking, hydroconversion, hydrotreatment, hydrodesulfurization and hydrodenitrogenation, catalytic elimination of nitrogen oxides, said reactions involving feeds comprising saturated and unsaturated aliphatic hydrocarbons, aromatic hydrocarbons, oxygen-containing organic compounds and organic compounds containing nitrogen and/or sulfur, as well as organic compounds containing other functional groups. More preferably, the material according to the invention is used as a catalyst in catalytic cracking reactions of hydrocarbon-containing molecules, notably cumene. These cracking reactions are carried out at a temperature ranging between 150° C. and 450° C., at atmospheric pressure and with a carrier gas ($N_2$ for example) flow rate ranging between 24 and 72 l/h/g catalyst. The carrier gas can also be helium. Preferably, the carrier gas $N_2$ flow rate ranges between 45 and 65 l/h/g catalyst and the cumene partial pressure is constant, preferably ranging between 650 and 850 Pa. As regards cumene cracking, the material according to the invention achieves optimum conversion of cumene to benzene and propene.

The invention is illustrated by the following examples.

EXAMPLES

In the examples hereafter, the aerosol technique used is the technique described above in the description of the invention.

For each one of Examples 1 to 5 below, the $V_{inorganic}/V_{organic}$ ratio of the mixture from stage b) is calculated. This ratio is defined as follows: $V_{inorganic}/V_{organic} = (m_{inorg} * \rho_{org})/(m_{org} * \rho_{inorg})$ with $m_{inorg}$ the final mass of the inorganic fraction in form of condensed oxide(s), i.e. $SiO_2$ and $AlO_2$, in the solid elementary particle, $m_{org}$ the total mass of the non-volatile organic fraction found in the solid elementary particle, i.e. the surfactant and the structuring agent, $\rho_{org}$ and $\rho_{inorg}$ the densities respectively associated with the non-volatile organic and inorganic fractions. In the following examples, we consider that $\rho_{org}=1$ and $\rho_{inorg}=2$. Thus, the $V_{inorganic}/V_{organic}$ ratio is calculated as equal to $V_{inorganic}/V_{organic} = (m_{SiO2}+m_{AlO2})/[2*(m_{structuring\ agent}+m_{surfactant})]$. Ethanol, soda and water are not taken into account in the calculation of said $V_{inorganic}/V_{organic}$ ratio.

Example 1 (Invention)

Preparation of a Material with Mesoporous and Macroporous Porosity Whose Microporous Amorphous Walls Consist of ZSM-5 (MFI) Zeolite Seeds Such that Molar Ratio Si/Al=10

10.05 g of a tetrapropylammonium hydroxide solution (TPAOH 20% by mass in an aqueous solution) are added to 4.3 g of demineralized water and 9.2 mg of sodium hydroxide NaOH. The mixture is left under stirring for 10 minutes. 0.7 g of aluminium sec-butoxide ($Al(O^sC_4H_9)_3$) is then added. Hydrolysis of the aluminic precursor is carried out for 1 hour. 6 g of tetraethylorthosilicate (TEOS) are then added. The mixture is kept under stirring for 18 hours at ambient temperature so as to obtain a clear solution. 18 ml of this solution are then added to a solution containing 35.2 g ethanol, 11.3 g water and 2 g surfactant F127 (pH value of the mixture=10.5). The $V_{inorganic}/V_{organic}$ ratio of the mixture is 0.21 and it is calculated as described above. The mixture is left under stirring for 10 minutes. It is then sent to the atomization chamber of the aerosol generator as described in the description above and the solution is sprayed in form of fine droplets under the action of the carrier gas (dry air) introduced under pressure (P=1.5 bar). The droplets are dried according to the protocol mentioned in the description above: they are conveyed via an $O_2/N_2$ mixture in PVC tubes. They are then fed into an oven set at a drying temperature of 250° C. The powder collected is then dried for 12 hours in a stove at 95° C. The powder is thereafter calcined in air for 5 hours at 550° C. The powder thus obtained is then suspended in an aqueous $NH_4NO_3$ solution (1 mol/l) for 2 h 30 at ambient temperature, then for 1 hour at 60° C. under stirring. After filtering (9000 rpm centrifugation) and washing with demineralized water, the powder is again dried in the stove at 60° C. and calcined in air for 5 hours at 550° C. The solid is characterized by nitrogen volumetric analysis, mercury porosimetry, TEM, SEM, XF. The TEM analysis shows that the spherical particles that make up the material exhibit a core macroporosity characterized by 300 to 500-nm long and 100 to 200-nm wide domains, and a mesoporosity on the periphery of the particles characterized by 20 to 50-nm domains, the whole being characteristic of an organic-inorganic phase separation obtained by a spinodal decomposition mechanism present before the calcination stage. Nitrogen volumetric analysis combined with the $\alpha_s$ method analysis leads to a value of the micropore volume $V_{micro}$ of 0.04 ml/g ($N_2$), a value of the mesopore volume $V_{meso}$ of 0.23 ml/g ($N_2$) and a specific surface area of the final material S=178 m²/g. The macroporous mercury volume defined by mercury porosimetry is 0.20 ml/g (the value of the mesoporous mercury volume also obtained by mercury porosimetry is in total accordance with the value obtained by nitrogen volumetric analysis). The Si/Al molar ratio obtained by XF is 10. A SEM image of the spherical elementary particles thus obtained shows that these particles have a size characterized by a diameter ranging between 50 and 700 nm, the size distribution of these particles being around 300 nm.

Example 2 (Invention)

Preparation of a Material with Mesoporous and Macroporous Porosity Whose Microporous Amorphous Walls Consist of ZSM-5 (MFI) Zeolite Seeds Such that Molar Ratio Si/Al=4

10.05 g of a tetrapropylammonium hydroxide solution (TPAOH 20% by mass in an aqueous solution) are added to 4.3 g of demineralized water and 9.2 mg of sodium hydroxide NaOH. The mixture is left under stirring for 10 minutes. 1.75 g of aluminium sec-butoxide (Al(O$^s$C$_4$H$_9$)$_3$) is then added. Hydrolysis of the aluminic precursor is carried out for 1 hour. 6 g of tetraethylorthosilicate (TEOS) are then added. The mixture is kept under stirring for 18 hours at ambient temperature so as to obtain a clear solution. 18 ml of this solution are then added to a solution containing 35.2 g ethanol, 11.3 g water and 2 g surfactant F127 (pH value of the mixture=10.5). The $V_{inorganic}/V_{organic}$ ratio of the mixture is 0.235 and it is calculated as described above. The mixture is left under stirring for 10 minutes. It is then sent to the atomization chamber of the aerosol generator as described in the description above and the solution is sprayed in form of fine droplets under the action of the carrier gas (dry air) introduced under pressure (P=1.5 bar). The droplets are dried according to the protocol mentioned in the description above: they are conveyed via an $O_2/N_2$ mixture in PVC tubes. They are then fed into an oven set at a drying temperature of 250° C. The powder collected is then dried for 12 hours in a stove at 95° C. The powder is thereafter calcined in air for 5 hours at 550° C. The powder thus obtained is then suspended in an aqueous NH$_4$NO$_3$ solution (1 mol/l) for 2 h 30 at ambient temperature, then for 1 hour at 60° C. under stirring. After filtering (9000 rpm centrifugation) and washing with demineralized water, the powder is again dried in the stove at 60° C. and calcined in air for 5 hours at 550° C. The solid is characterized by nitrogen volumetric analysis, mercury porosimetry, TEM, SEM, XF. The TEM analysis shows that the spherical particles that make up the material exhibit a core macroporosity characterized by 300 to 500-nm long and 100 to 200-nm wide domains, and a mesoporosity on the periphery of the particles characterized by 20 to 50-nm domains, the whole being characteristic of an organic-inorganic phase separation obtained by a spinodal decomposition mechanism present before the calcination stage. Nitrogen volumetric analysis combined with the $\alpha_s$ method analysis leads to a value of the micropore volume $V_{micro}$ of 0.03 ml/g ($N_2$), a value of the mesopore volume $V_{meso}$ of 0.19 ml/g ($N_2$) and a specific surface area of the final material S=130 m²/g. The macroporous mercury volume defined by mercury porosimetry is 0.13 ml/g (the value of the mesoporous mercury volume also obtained by mercury porosimetry is in total accordance with the value obtained by nitrogen volumetric analysis). The Si/Al molar ratio obtained by XF is 4. A SEM image of the spherical elementary particles thus obtained shows that these particles have a size characterized by a diameter ranging between 50 and 700 nm, the size distribution of these particles being around 300 nm.

Example 3 (Invention)

Preparation of a Material with Mesoporous and Macroporous Porosity Whose Microporous Amorphous Walls Consist of Silicalite (MFI) Seeds 10.05 g of a tetrapropylammonium hydroxide solution (TPAOH 20% by mass in an aqueous solution) are added to 4.3 g of demineralized water and 9.2 mg of sodium hydroxide NaOH. The mixture is left under stirring for 10 minutes. 6 g of tetraethylorthosilicate (TEOS) are then added. The mixture is kept under stirring for 18 hours at ambient temperature so as to obtain a clear solution. 18 ml of this solution are then added to a solution containing 35.2 g ethanol, 11.3 g water and 2 g surfactant F127 (pH value of the mixture=10.5). The $V_{inorganic}/V_{organic}$ ratio of the mixture is 0.20 and it is calculated as described above. The mixture is left under stirring for 10 minutes. It is then sent to the atomization chamber of the aerosol generator as described in the description above and the solution is sprayed in form of fine droplets under the action of the carrier gas (dry air) introduced under pressure (P=1.5 bar). The droplets are dried according to the protocol mentioned in the description above: they are conveyed via an $O_2/N_2$ mixture in PVC tubes. They are then fed into an oven set at a drying temperature of 250° C. The powder collected is then dried for 12 hours in a stove at 95° C. The powder is then calcined in air for 5 hours at 550° C. The solid is characterized by nitrogen volumetric analysis, mercury porosimetry, TEM, SEM. The TEM analysis shows that the spherical particles that make up the material exhibit a core macroporosity characterized by 300 to 500-nm long and 100 to 200-nm wide domains, and a mesoporosity on the periphery of the particles characterized by 20 to 50-nm domains, the whole being characteristic of an organic-inorganic phase separation obtained by a spinodal decomposition mechanism present before the calcination stage. Nitrogen volumetric analysis combined with the $\alpha_s$ method analysis leads to a value of the micropore volume $V_{micro}$ of 0.3 ml/g ($N_2$), a value of the mesopore volume $V_{meso}$ of 0.5 ml/g ($N_2$) and a specific surface area of the final material S=620 m²/g. The macroporous mercury volume defined by mercury porosimetry is 0.4 ml/g (the value of the mesoporous mercury volume also obtained by mercury porosimetry is in total accordance with the value obtained by nitrogen volumetric analysis). A SEM image of the spherical elementary particles thus obtained shows that these particles have a size characterized by a diameter ranging between 50 and 700 nm, the size distribution of these particles being around 300 nm.

Example 4 (Invention)

Preparation of a Material with Mesoporous and Macroporous Porosity Whose Microporous Amorphous Walls Consist of Beta (BEA) Zeolite Seeds Such that the Molar Ratio Si/Al=50

11.70 g of a tetraethylammonium hydroxide solution (TEAOH 20% by mass in an aqueous solution) are added to 7.8 g of demineralized water and 0.03 g of sodium hydroxide NaOH. The mixture is left under stirring for 10 minutes. 0.14 g of aluminium sec-butoxide $(Al(O^sC_4H_9)_3)$ is then introduced. The mixture is left under stirring for 10 minutes. Hydrolysis of the aluminic precursor is carried out for 1 hour. 6 g of tetraethylorthosilicate (TEOS) are then added. The mixture is kept under stirring for 18 hours at ambient temperature so as to obtain a clear solution. 18 ml of this solution are then added to a solution containing 35.2 g ethanol, 11.3 g water and 2 g surfactant F127 (pH value of the mixture=10). The $V_{inorganic}/V_{organic}$ ratio of the mixture is 0.17 and it is calculated as described above. The mixture is left under stirring for 10 minutes. It is then sent to the atomization chamber of the aerosol generator as described in the description above and the solution is sprayed in form of fine droplets under the action of the carrier gas (dry air) introduced under pressure (P=1.5 bar). The droplets are dried according to the protocol mentioned in the description above: they are conveyed via an $O_2/N_2$ mixture in PVC tubes. They are then fed into an oven set at a drying temperature of 250° C. The powder collected is dried for 12 hours in a stove at 95° C. The powder is then calcined in air for 5 hours at 550° C. The powder thus obtained is then suspended in an aqueous $NH_4NO_3$ solution (1 mol/l) for 2 h 30 at ambient temperature, then for 1 hour at 60° C. under stirring. After filtering (9000 rpm centrifugation) and washing with demineralized water, the powder is again dried in the stove at 60° C. and calcined in air for 5 hours at 550° C. The solid is characterized by nitrogen volumetric analysis, mercury porosimetry, TEM, SEM, XF. The TEM analysis shows that the spherical particles that make up the material exhibit a core macroporosity characterized by 200 to 500-nm long and 100 to 200-nm wide domains, and a mesoporosity on the periphery of the particles characterized by 20 to 50-nm domains, the whole being characteristic of an organic-inorganic phase separation obtained by a spinodal decomposition mechanism present before the calcination stage. Nitrogen volumetric analysis combined with the $\alpha_s$ method analysis leads to a value of the micropore volume $V_{micro}$ of 0.1 ml/g ($N_2$), a value of the mesopore volume $V_{meso}$ of 0.5 ml/g ($N_2$) and a specific surface area of the final material S=200 m²/g. The macroporous mercury volume defined by mercury porosimetry is 0.2 ml/g (the value of the mesoporous mercury volume also obtained by mercury porosimetry is in total accordance with the value obtained by nitrogen volumetric analysis). The Si/Al molar ratio obtained by XF is 50. A SEM image of the spherical elementary particles thus obtained shows that these particles have a size characterized by a diameter ranging between 50 and 700 nm, the size distribution of these particles being around 300 nm.

Example 5 (Invention)

Preparation of a Material with Mesoporous and Macroporous Porosity Whose Microporous Amorphous Walls Consist of Y (FAU) Zeolite Seeds Such that the Molar Ratio Si/Al=8

0.41 g of sodium aluminate ($NaAlO_2$) is added to a solution containing 0.17 g sodium hydroxide and 7.6 g of demineralized water. The solution is left under stirring until the aluminium precursor is dissolved. 10 g of sodium silicate (27% by weight of $SiO_2$ and 14% NaOH) are then added under vigorous stirring. The mixture is kept under stirring for 18 hours at ambient temperature so as to obtain a clear solution. 15 ml of this solution are then added to a solution containing 35.2 g ethanol, 11.6 g water and 6.3 g surfactant F127 (pH value of the mixture=9.8). The $V_{inorganic}/V_{organic}$ ratio of the mixture is 0.24 and it is calculated as described above. The mixture is left under stirring for 10 minutes. It is then sent to the atomization chamber of the aerosol generator as described in the description above and the solution is sprayed in form of fine droplets under the action of the carrier gas (dry air) introduced under pressure (P=1.5 bar). The droplets are dried according to the protocol mentioned in the description above: they are conveyed via an $O_2/N_2$ mixture in PVC tubes. They are then fed into an oven set at a drying temperature of 250° C. The powder collected is thereafter dried for 12 hours in a stove at 95° C. The powder is then calcined in air for 5 hours at 550° C. The powder thus obtained is then suspended in an aqueous $NH_4NO_3$ solution (1 mol/l) for 2 h 30 at ambient temperature, then for 1 hour at 60° C. under stirring. After filtering (9000 rpm centrifugation) and washing with demineralized water, the powder is again dried in the stove at 60° C. and calcined in air for 5 hours at 550° C. The solid is characterized by nitrogen volumetric analysis, mercury porosimetry, TEM, SEM and XF. The TEM analysis shows that the spherical particles that make up the material exhibit a core macroporosity characterized by 200 to 500-nm long and 100 to 200-nm wide domains, and a mesoporosity on the periphery of the particles characterized by 20 to 50-nm domains, the whole being characteristic of an organic-inorganic phase separation obtained by a spinodal decomposition mechanism present before the calcination stage. Nitrogen volumetric analysis combined with the $\alpha_s$ method analysis leads to a value of the micropore volume $V_{micro}$ of 0.25 ml/g ($N_2$), a value of the mesopore volume $V_{meso}$ of 0.7 ml/g ($N_2$) and a specific surface area of the final material S=380 m²/g. The macroporous mercury volume defined by mercury porosimetry is 0.3 ml/g (the value of the mesoporous mercury volume also obtained by mercury porosimetry is in total accordance with the value obtained by nitrogen volumetric analysis). The Si/Al molar ratio obtained by XF is 8. A SEM image of the spherical elementary particles thus obtained shows that these particles have a size characterized by a diameter ranging between 50 and 700 nm, the size distribution of these particles being around 300 nm.

Example 6 (Invention)

Cracking of the Cumene Catalyzed by the Material of Example 1 According to the Invention 50 mg of powder of the material of Example 1 are placed in a reactor. The powder is pretreated at 500° C. for 2 hours, then at 300° C. for 11 h under nitrogen. The cumene, maintained at 14° C., is conveyed through the powder by a nitrogen stream with a flow rate of 60 l/h/g solid tested. The reaction temperature is set at 300° C. The reaction is carried out under atmospheric pressure. The reaction products are analyzed by means of a Perichrom 2100 chromatograph. The conversion rate of the cracking reaction of cumene to propene and benzene depends on the Brönsted acidity properties of the solid tested. The conversion rate per unit of mass of the material of Example 1 is 32% (±5%). The conversion rate per unit of specific surface area (100 m²/g) of the material of Example 1 is 18%.

Example 7 (Invention)

Cracking of the Cumene Catalyzed by the Material of Example 2 According to the Invention 50 mg of powder of the material of Example 2 are placed in a reactor. The powder is pretreated at 500° C. for 2 hours, then at 300° C. for 11 h under nitrogen. The cumene, maintained at 14° C., is conveyed through the powder by a nitrogen stream with a flow rate of 60 l/h/g solid tested. The reaction temperature is set at 300° C. The reaction is carried out under atmospheric pressure. The reaction products are analyzed by means of a Perichrom 2100 chromatograph. The conversion rate of the cracking reaction of cumene to propene and benzene depends on the Brönsted acidity properties of the solid tested. The conversion rate per unit of mass of the material of Example 2 is 37%. The conversion rate per unit of specific surface area (100 m²/g) of the material of Example 2 is 30%.

Example 8 (Comparative Example)

Cracking of the Cumene Catalyzed by a Grace Davison Commercial Amorphous Aluminosilicate, Si/Al=4, $S_{BET}$=365 m²/g 50 mg of powder of the commercial aluminosilicate are placed in a reactor. The powder is pretreated at 500° C. for 2 hours, then at 300° C. for 11 h under nitrogen. The cumene, maintained at 14° C., is conveyed through the powder by a nitrogen stream with a flow rate of 60 l/h/g solid tested. The reaction temperature is set at 300° C. The reaction is carried out under atmospheric pressure. The reaction products are analyzed by means of a Perichrom 2100 chromatograph. The conversion rate of the cracking reaction of cumene to propene and benzene depends on the Brönsted acidity properties of the solid tested. The conversion rate per unit of mass of the commercial aluminosilicate is 12% (±5%). The conversion rate per unit of specific surface area (100 m²/g) of the commercial aluminosilicate is 3%.

The invention claimed is:

1. A material with hierarchical porosity containing at least two elementary spherical particles having a maximum diameter of 200 microns, said elementary spherical particles being devoid of zeolite nanocrystals, at least one of said spherical particles comprising at least one matrix based on silicon oxide and having amorphous walls, said material having a macropore volume measured by mercury porosimetry ranging between 0.05 and 1 ml/g, a mesopore volume measured by nitrogen volumetric analysis ranging between 0.01 and 1 ml/g and a micropore volume measured by nitrogen volumetric analysis ranging between 0.03 and 0.4 ml/g.

2. A material as claimed in claim 1, wherein the macropore volume measured by mercury porosity is between 0.1 and 0.3 ml/g.

3. A material as claimed in claim 1, wherein the mesopore volume measured by nitrogen volumetric analysis is between 0.1 and 0.6 ml/g.

4. A material as claimed in claim 1, wherein the macroporosity is present in domains between 50 and 1000 nm.

5. A material as claimed in claim 1, wherein the mesoporosity is present in domains between 2 and 50 nm.

6. A material as claimed in claim 1, which has elementary spherical particles devoid of mesoporosity.

7. A material as claimed in claim 1, wherein said matrix has amorphous walls consisting of zeolite seeds.

8. A material as claimed in claim 7, wherein said zeolite seeds are species for priming at least one MFI, BEA, FAU or LTA structural type zeolite.

9. A material as claimed in claim 1, wherein said matrix based on silicon oxide is entirely silicic.

10. A material as claimed in claim 1, wherein said matrix based on silicon oxide comprises at least one element X selected from the group consisting of aluminium, iron, boron, indium and gallium.

11. A material as claimed in claim 10, wherein element X is aluminium.

12. A material as claimed in claim 1, wherein said elementary spherical particles have a diameter between 50 nm and 10 microns.

13. A material as claimed in claim 1, which has a specific surface area between 100 and 1100 m²/g.

14. A material with hierarchical porosity as claimed in claim 1, which consists of at least two elementary spherical particles having a maximum diameter of 200 microns, said elementary spherical particles being devoid of zeolite nanocrystals, at least one of said spherical particles comprising at least one matrix based on silicon oxide and having amorphous walls, said material having a macropore volume measured by mercury porosimetry between 0.05 and 1 ml/g, a mesopore volume measured by nitrogen volumetric analysis between 0.01 and 1 ml/g and a micropore volume measured by nitrogen volumetric analysis between 0.03 and 0.4 ml/g.

15. A material as claimed in claim 14, wherein said matrix has amorphous walls consisting of zeolite seeds.

16. An adsorbent, comprising the material with hierarchical porosity as claimed in claim 1.

17. A catalyst, comprising the material with hierarchical porosity as claimed in claim 1.

18. A method of preparing the material as claimed in claim 1, comprising:
   a) preparing a clear solution containing the precursor elements of zeolite seeds, at least one silicic precursor and optionally at least one precursor of at least one element X selected from the group consisting of aluminum, iron, boron, indium and gallium;
   b) mixing into a solution at least one surfactant and at least said clear solution obtained in a);
   c) aerosol atomizing said solution obtained in b) so as to lead to the formation of spherical droplets;
   d) drying said droplets; and
   e) eliminating said precursor elements of zeolite seeds and said surfactant so as to obtain the material with hierarchal porosity in the microporosity, mesoporosity and macroporosity domains.

19. A method as claimed in claim 18, wherein element X is aluminium.

20. A method as claimed in claim 18, wherein said surfactant is a three-block copolymer, each block consisting of a poly(alkylene oxide) chain.

21. A method as claimed in claim 20, wherein said three-block copolymer consists of two poly(ethylene oxide) chains and of one poly(propylene oxide) chain.

* * * * *

UNITED STATES PATENT AND TRADEMARK OFFICE
CERTIFICATE OF CORRECTION

PATENT NO.       : 8,673,253 B2
APPLICATION NO.  : 12/676707
DATED            : March 18, 2014
INVENTOR(S)      : Chaumonnot et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1046 days.

Signed and Sealed this
Twenty-ninth Day of September, 2015

Michelle K. Lee
*Director of the United States Patent and Trademark Office*